(12) United States Patent
Wiedmann et al.

(10) Patent No.: US 9,888,894 B2
(45) Date of Patent: Feb. 13, 2018

(54) MULTI-ENERGY X-RAY IMAGING

(71) Applicant: General Electric Company, Schenectady, NY (US)

(72) Inventors: Uwe Wiedmann, Clifton Park, NY (US); Peter Michael Edic, Albany, NY (US); Bruno Kristiaan Bernard De Man, Clifton Park, NY (US); Naveen Stephan Chandra, Salt Lake City, UT (US); Jed Douglas Pack, Glenville, NY (US); Yannan Jin, Schenectady, NY (US); Denis Perrillat-Amede, Buc (FR); Jean-Francois Larroux, Buc (FR)

(73) Assignee: General Electric Company, Niskayuna, NY (US)

( * ) Notice: Subject to any disclaimer, the term of this patent is extended or adjusted under 35 U.S.C. 154(b) by 121 days.

(21) Appl. No.: 14/977,086

(22) Filed: Dec. 21, 2015

(65) Prior Publication Data

US 2017/0172528 A1 Jun. 22, 2017

(51) Int. Cl.
*A61B 6/00* (2006.01)
*A61B 6/03* (2006.01)

(52) U.S. Cl.
CPC .............. *A61B 6/482* (2013.01); *A61B 6/032* (2013.01); *A61B 6/5258* (2013.01)

(58) Field of Classification Search
CPC ......... A61B 6/482; A61B 6/032; A61B 6/405; A61B 6/5205; A61B 6/027; A61B 6/4241; A61B 6/481; A61B 6/488; A61B 6/4035; A61B 6/583; A61B 6/54; A61B 6/035; A61B 6/4021; A61B 6/52; A61B 6/5258; A61B 6/542; A61B 6/504; A61B 5/4869; G01N 23/046; G01N 2223/0766; G01N 2223/419; G01N 2223/612;
(Continued)

(56) References Cited

U.S. PATENT DOCUMENTS 7,431,500 B2 10/2008 Deych et al.
7,813,474 B2 10/2010 Wu et al.
(Continued)

FOREIGN PATENT DOCUMENTS

WO 2013190435 A1 12/2013

OTHER PUBLICATIONS

Granton, P.V., et al.; "Implementaqtion of dual- and triple-energy cone-beam micro-CT for postreconstruction material decomposition"; Meical Physics vol. 35, Issue No. 11, Nov. 2008; pp. 5030-5042.
(Continued)

*Primary Examiner* — Irakli Kiknadze
(74) *Attorney, Agent, or Firm* — Pabrita K. Chakrabarti

(57) ABSTRACT

Acquisition of X-ray transmission data at three or more energy levels is described. Various implementations utilize generator waveforms that utilize fast-switching, slow-switching, or a combination of fast- and slow-switching to transition between X-ray energy levels. In addition, various sampling arrangements for sampling and/or binning three or more energy levels of X-ray transmission data are discussed. The use of these data in subsequent processing steps, such for material decomposition and/or improvement of dual-energy material decomposition processing, are also described.

17 Claims, 8 Drawing Sheets

(58) Field of Classification Search
CPC ........... G01N 2223/6126; G01N 23/04; G01N 23/223; G01N 23/2251; G01V 5/0033; G01V 5/0069; G01V 5/0041; G01V 5/005; A61K 2039/5158; A61K 2039/55505; A61K 2039/55566; A61K 2039/6006; A61K 39/00; G01T 1/171; G01T 7/08
USPC .......................................... 378/4, 5, 9, 19, 62
See application file for complete search history.

(56) References Cited

U.S. PATENT DOCUMENTS

| | | | |
|---|---|---|---|
| 8,155,263 B2 | 4/2012 | Wu et al. | |
| 8,515,147 B2 | 8/2013 | Baeumer et al. | |
| 8,855,385 B2 | 10/2014 | Kriston et al. | |
| 9,020,092 B2 | 4/2015 | Wang et al. | |
| 2004/0264626 A1* | 12/2004 | Besson | A61B 6/508 378/4 |
| 2011/0019891 A1* | 1/2011 | Puong | A61B 6/405 382/131 |
| 2011/0280367 A1* | 11/2011 | Baeumer | A61B 6/032 378/9 |
| 2013/0202178 A1 | 8/2013 | Shechter | |
| 2014/0270055 A1* | 9/2014 | Oikawa | A61B 6/405 378/16 |
| 2015/0170358 A1 | 6/2015 | Hamann et al. | |
| 2015/0351715 A1* | 12/2015 | Ota | A61B 6/4233 378/64 |
| 2016/0095561 A1* | 4/2016 | Tamura | A61B 6/032 378/62 |

OTHER PUBLICATIONS

Huh, Wonseok, et al.; "Fast KVP-Switching Dual Energy CT for PET Attenuation Correction"; Nuclear Science Symposium Conference Record Oct. 24-Nov. 1, 2009; pp. 2510-2515.

Long, Yong, et al.; "Multi-Material Decomposition Using Statistical Image Reconstruction for Spectral CT"; Medical Imaging vol. 33, Issue No. 8, Aug. 2014, pp. 1614-1626.

* cited by examiner

MULTI-ENERGY X-RAY IMAGING

BACKGROUND

The subject matter disclosed herein relates to multi-energy X-ray imaging.

Non-invasive imaging technologies allow images of the internal structures or features of a patient to be obtained without performing an invasive procedure on the patient. In particular, such non-invasive imaging technologies rely on various physical principles, such as the differential transmission of X-rays through the target volume or the reflection of acoustic waves, to acquire data and to construct images or otherwise represent the observed internal features of the patient.

For example, in computed tomography (CT) and other X-ray-based imaging technologies, X-ray radiation spans a subject of interest, such as a human patient, and a portion of the radiation impacts a detector where the intensity data is collected. In digital X-ray systems a photo detector produces signals representative of the amount or intensity of radiation impacting discrete pixel regions of a detector surface. The signals may then be processed to generate an image that may be displayed for review. In CT systems, a detector array, including a series of detector elements, produces similar signals through various positions as a gantry is rotated around a patient.

In the images produced by such systems, it may be possible to identify and examine the internal structures and organs within a patient's body. It may also be desirable to characterize the tissues or agents that are present in the imaged volume, such as based on tissue type or the presence or absence of a chemical or molecule of interest, such as a contrast agent. However, in practice, such characterization may be difficult to achieve. In particular, although materials have a distinct attenuation profile as a function of energy, tissue separation in practice is not a trivial operation as tissues are a mixture of different materials with a range of densities that vary across subjects.

Such material separation may be more effectively implemented to the extent that data can be acquired at multiple, distinct energy spectra. Conventionally, systems are configured to acquire data using only two energy spectra (i.e., a high-energy spectrum and a low-energy spectrum). Material separation may, therefore, be limited to what can be achieved using two fixed spectra.

In the following description, the spectra are generally characterized by the maximum operating voltage of the X-ray tube (kVp), also denoted as the operating voltage level of the X-ray tube. Though such X-ray emissions may be generally described or discussed herein as being at a particular energy level (e.g., referring to the electron beam energy level in a tube with an operating voltage of 80 kVp, 140 kVp, and so forth), the respective X-ray emissions actually comprise a continuum or spectrum of energies and may, therefore, constitute a polychromatic emission centered at, terminating at, or having a peak strength at, the target energy.

BRIEF DESCRIPTION

In one implementation, an X-ray generator waveform used in the generation of X-rays and having at least three distinct energy levels is provided. In accordance with this implementation, the X-ray generator waveform includes: a low-energy region having a substantially constant low operating voltage value for at least a first duration; at least one intermediate-energy region having a substantially constant intermediate operating voltage value for at least a second duration; and a high-energy region having a substantially constant high operating voltage value for at least a third duration.

In a further implementation, a method for sampling X-ray data is provided. In accordance with this implementation, X-rays are generated in accordance with an X-ray generator waveform having an operating voltage rise and decay cycle that is repeated over time. During each operating voltage rise and decay cycle, data is sampled during at least three separate and distinct data sampling voltage intervals.

In an additional implementation, a method for generating material decomposition images is provided. In accordance with this implementation, X-ray transmission data is acquired at a low-energy, a high-energy, and an intermediate-energy. One or more material decomposition images are generated using the X-ray transmission data acquired at the low-energy and the high-energy. At least one material decomposition image is corrected with the data acquired at the intermediate-energy.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
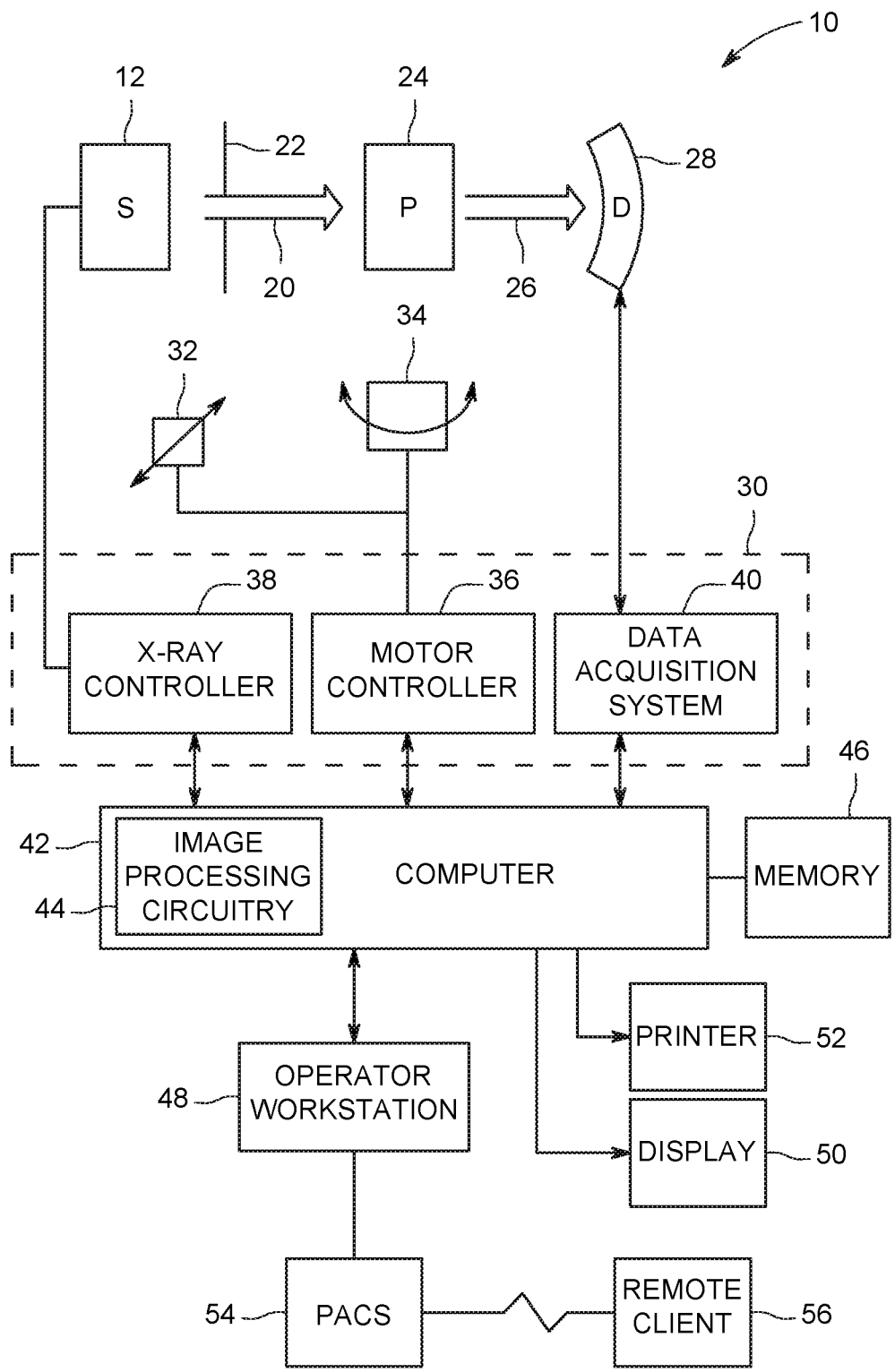
FIG. 1 is a schematic illustration of an embodiment of a computed tomography (CT) system configured to acquire CT images of a patient and process the images in accordance with aspects of the present disclosure.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While the following discussion is generally provided in the context of medical imaging, it should be appreciated that the present techniques are not limited to such medical contexts. Indeed, the provision of examples and explanations in such a medical context is only to facilitate explanation by providing instances of real-world implementations and applications. However, the present approaches may also be utilized in other contexts, such as the non-destructive inspection of manufactured parts or goods (i.e., quality control or quality review applications), and/or the non-invasive inspection of packages, boxes, luggage, and so forth (i.e., security or screening applications). In general, the present approaches may be desirable in any imaging or screening context in which material decomposition, or otherwise acquiring imaging data at multiple energy spectra, is desirable.

Tissue characterization or classification may be desirable in various clinical contexts to assess the tissue being characterized for pathological conditions and/or to assess the tissue for the presence of various elements, chemicals or molecules of interest. However, tissue characterization in imaging studies, such as using computed tomography (CT), may be problematic due to tissues being a mixture of different materials with range of densities that vary across subjects. In particular, conventional approaches typically use dual-energy approaches (i.e., data acquisition at a high-energy spectrum and a low-energy spectrum), which may be insufficient to discriminate between materials at many locations. However, generation of additional X-ray spectra may be impractical in conventional systems due to the increased X-ray tube and/or driver complexity that may be entailed, the potential decrease in temporal resolution due to longer data acquisition times, and/or the potential increase in patient dose. Further, many conventional systems which may already be in place may be designed or otherwise configured with dual-energy data acquisitions in mind, and thus may have hardware or components specifically designed for X-ray emissions or data acquisitions using two energy levels. The approaches discussed herein address one or more of these concerns to allow X-ray transmission data to be acquired at three or more energy levels or spectra (e.g., three or more kVp), even in systems originally designed for dual-energy data acquisition.

Prior to discussing certain approaches for improving material decomposition applications, it may be useful to understand the operation and components of an imaging system that may be used to acquire such data. With this in mind, FIG. 1 illustrates an embodiment of an imaging system 10 for acquiring and processing image data in accordance with aspects of the present disclosure. In the illustrated embodiment, system 10 is a computed tomography (CT) system designed to acquire X-ray projection data at multiple energy spectra, to reconstruct the projection data into volumetric reconstructions, and to process the image data, including material decomposition or tissue-type image data, for display and analysis. The CT imaging system 10 includes one or more X-ray sources 12, such as one or more X-ray tubes or solid state emission structures which allow X-ray generation at multiple spectra having different energy characteristics, during the course of an imaging session. For example, the emission spectra may differ in one or more of their mean, median, mode, maximum, or minimum X-ray energies.

By way of example, in one embodiment an X-ray source 12 (e.g., an X-ray tube) may be switched between a relatively low-energy polychromatic emission spectrum (e.g., X-ray tube operating voltage at about 80 kVp) and a relatively high-energy polychromatic emission spectrum (e.g., at about 140 kVp), with a transition between the high- and low-energy spectra allowing acquisition of projections at an intermediate or transitional energy polychromatic emission spectrum between the low- and the high-energy spectra (e.g., X-ray tube operating voltage between 80 kVp and 140 kVp). As will be appreciated, the X-ray source(s) 12 may emit at polychromatic spectra localized around energy levels (i.e., spectra induced by specific kVp ranges) other than those listed herein. Indeed, selection of the respective energy levels for emission may be based, at least in part, on the anatomy being imaged and the chemical or molecules of interest for tissue characterization.

In certain implementations, the source 12 may be positioned proximate to a beam shaper 22 used to define the size and shape of the one or more X-ray beams 20 that pass into a region in which a subject 24 (e.g., a patient) or object of interest is positioned. The subject 24 attenuates at least a portion of the X-rays. Resulting attenuated X-rays 26 impact a detector array 28 formed by a plurality of detector elements (e.g., a one-dimensional or two-dimensional detector array). Each detector element produces an electrical signal that represents the intensity of the X-ray beam incident at the position of the detector element when the beam strikes the detector 28. Electrical signals are acquired and processed to generate one or more scan datasets.

A system controller 30 commands operation of the imaging system 10 to execute examination protocols and to pre-process or process the acquired data. With respect to the X-ray source(s) 12, the system controller 30 furnishes power, focal spot location, control signals and so forth, for the X-ray examination sequences. The detector 28 is coupled to the system controller 30, which commands acquisition of the signals generated by the detector 28. In addition, the system controller 30, via a motor controller 36, may control operation of a linear positioning subsystem 32 and/or a rotational subsystem 34 used to move components of the imaging system 10 and/or the subject 24.

The system controller 30 may include signal processing circuitry and associated memory circuitry. In such embodiments, the memory circuitry may store programs, routines, and/or encoded algorithms executed by the system controller 30 to operate the imaging system 10, including the X-ray source 12 and detector 28, such as to generate and/or acquire X-ray transmission data at three or more energy levels or bins, as well as to process the data acquired by the detector 28. In one embodiment, the system controller 30 may be implemented as all or part of a processor-based system such as a general-purpose or application-specific computer system.

The source(s) 12 may be controlled by an X-ray controller 38 contained within the system controller 30. The X-ray controller 38 may be configured to provide power and timing signals to the source(s) 12. In addition, in some embodiments the X-ray controller 38 may be configured to selectively activate the source(s) 12 such that tubes or emitters at different locations within the system 10 may be operated in synchrony with one another or independent of one another.

As discussed herein, in certain implementations discussed herein, the X-ray controller 38 and/or the source(s) 12 may be configured to provide fast-switching (i.e., near-instantaneous) switching of an X-ray source 12 between energy levels. In this manner, the X-ray emissions may be rapidly or near-instantly switched between different kV's at which the source 12 is operated to emit X-rays at different respective polychromatic energy spectra in succession or alternation during an image acquisition session. For example, in a triple-energy imaging context, the X-ray controller 38 may operate an X-ray source 12 so that the X-ray source 12 successively emits X-rays at different polychromatic energy spectra of interest, such that adjacent projections are acquired at different energies (i.e., a first projection is acquired at low-energy, a second projection is acquired at an intermediate-energy, a third projection is acquired at high-energy, and so forth). An example of one such fast-switching technology is distributed resonant energy recovery (DRER) which, when present in the system 10, may allow such fast-switching of the X-ray source(s) 12. Distributed resonant energy recovery is discussed in greater detail in U.S. Pat. No. 8,861,681, titled "Method and System for Active Resonant Voltage Switching" and filed on Dec. 17, 2010 to General Electric Company, which is herein incorporated by reference in its entirety for all purposes. In other implementations, however, such fast-switching technology may be absent, and a gradual or measurable transition may occur when switching between X-ray emission spectra.

The system controller 30 may include a data acquisition system (DAS) 40. The DAS 40 receives data collected by readout electronics of the detector 28, such as sampled digital or analog signals from the detector 28. The DAS 40 may then convert the data to digital signals for subsequent processing by a processor-based system, such as a computer 42. In other embodiments, the detector 28 may convert the sampled analog signals to digital signals prior to transmission to the data acquisition system 40.

In the depicted example, the computer 42 may include or communicate with one or more non-transitory memory devices 46 that can store data processed by the computer 42, data to be processed by the computer 42, or instructions to be executed by a processor of the computer 42. For example, a processor of the computer 42 may execute one or more sets of instructions stored on the memory 46, which may be a memory of the computer 42, a memory of the processor, firmware, or a similar instantiation. The memory 46 stores sets of instructions that, when executed by the processor, perform image acquisition and/or processing as discussed herein.

The computer 42 may also be adapted to control features enabled by the system controller 30 (i.e., scanning operations and data acquisition), such as in response to commands and scanning parameters provided by an operator via an operator workstation 48. The system 10 may also include a display 50 coupled to the operator workstation 48 that allows the operator to view relevant system data, imaging parameters, raw imaging data, reconstructed data, contrast agent density maps produced in accordance with the present disclosure, and so forth. Additionally, the system 10 may include a printer 52 coupled to the operator workstation 48 and configured to print any desired measurement results. The display 50 and the printer 52 may also be connected to the computer 42 directly or via the operator workstation 48. Further, the operator workstation 48 may include or be coupled to a picture archiving and communications system (PACS) 54. PACS 54 may be coupled to a remote client 56, radiology department information system (RIS), hospital information system (HIS) or to an internal or external network, so that others at different locations can gain access to the image data.

As noted above, the X-ray source(s) 12 may be configured to emit X-rays at multiple energy spectra, even if originally configured to emit X-rays at only two-energy spectra (e.g., high- and low-energy spectra). Though such emissions may be generally described or discussed as being at a particular energy level (e.g., referring to the electron beam energy in a tube with an operating voltage of 80 kVp, 140 kVp, and so forth), the respective X-ray emissions actually comprise a continuum or spectrum of energies and may, therefore, constitute a polychromatic emission centered at, terminating at, or having a peak strength at, the target energy. For the purpose of material decomposition, such differing emission spectra allow attenuation data to be obtained for the same anatomical regions at the different spectra, thereby allowing differential attenuation at the different spectra to be determined for a given material (or volume of material). Based on this differential attenuation at the known spectra, material decomposition techniques may be applied.

As discussed herein, in certain approaches an X-ray source 12 may be switched between low- and high-energy emitting states, with the resulting X-ray emission detected on a detector 28 opposite the source with respect to the imaged volume. During the transition between low- and high-energy states, additional data may be generated at a transitional or intermediate-energy or energy range between the low- and high-energy states that may also be of interest. This type of approach may yield high-, intermediate-, and low-energy transmission data that may be used in a material decomposition type imaging process. By way of explanation, certain of the following examples are presented in the context of generator waveforms illustrating changes in kVp over time for a multi-energy X-ray exposure. It should be appreciated, however, that instead of varying kVp alone, the described X-ray spectra can also be changed by varying the applied filtration, alone or in combination with kVp modulation.

Figure 2:
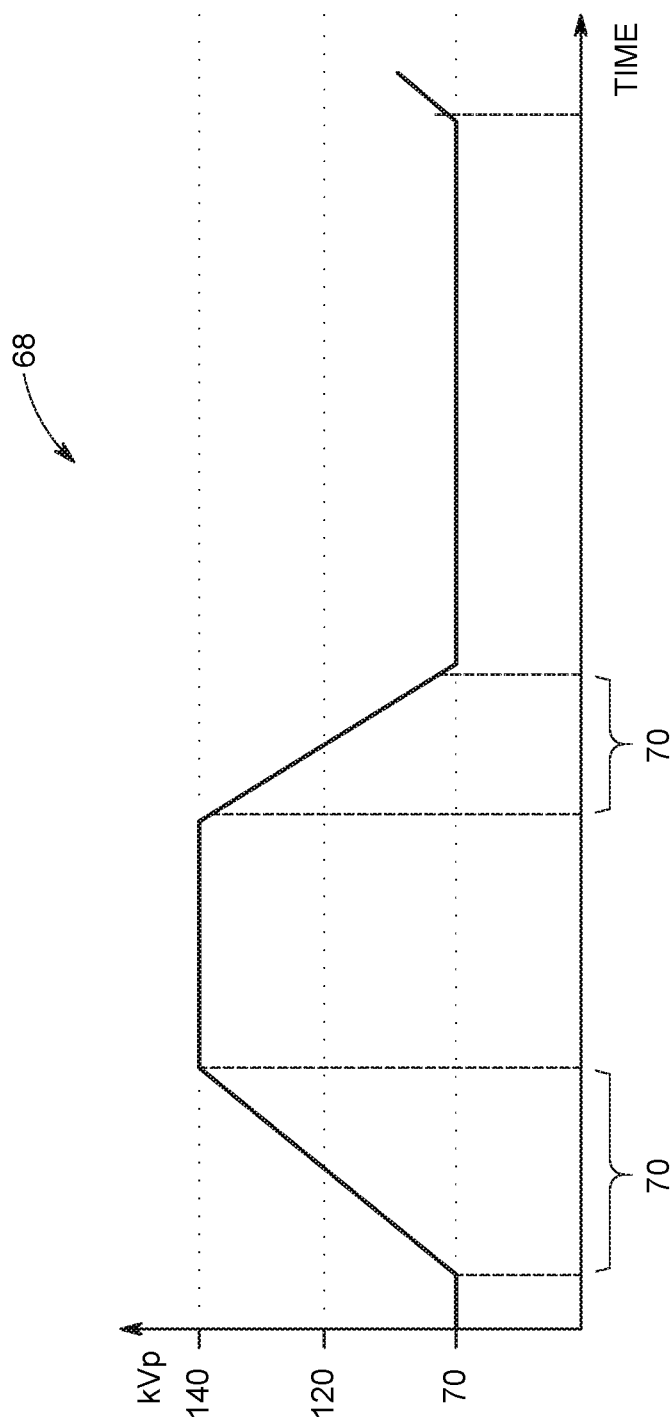
FIG. 2 depicts a slow-switched generator waveform in accordance with aspects of the present disclosure.

With the preceding in mind, and turning to FIG. 2, a first depiction of a generator waveform 68 is provided illustrating X-ray source 12 operating voltage in accordance with the present approaches. In this example, fast-switching of the X-ray source 12 is not provided, resulting in a gradual transition (represented by the sloped regions 70 of generator waveform 68) between low (e.g., 70 kVp) and high (e.g., 140 kVp) operating voltages. In operation, the gradual transition 70 between these two operating states (illustrated by a ramp up and ramp down between states) is effectively, at an intermediary operating voltage (e.g., 105 kVp-120 kVp) which, when sampled, would be representative of X-ray transmission at an intermediate-energy spectrum on average. Thus, projections acquired during one or both of the transition intervals 70 may be characterized as being at this intermediary voltage on average, effectively allowing these projections to be handled and processed as a third set of energy data acquired at an intermediate-energy. It should be noted that although the intermediate-energy spectrum is characterized by an intermediate operating voltage, this spectrum differs from a spectrum generated using a solitary tube operating voltage. Specifically, the spectra will contain photon energies above the intermediate operating voltage used to characterize the spectrum.

It may be noted that the generator waveform 68 illustrated in FIG. 2 may be considered as corresponding to a conventional dual-energy generator waveform, which can be generated using conventional switching technology (i.e., without fast-switching tube voltage capability). However, in a conventional dual-energy system, a break or transition point may be defined in the transition interval(s) 70, such as at a midpoint of the transition interval, with the respective data acquired on different sides of the transition point being binned as either high-energy or low-energy respectively. Unlike this conventional scenario, in certain presently contemplated implementations, the transitional interval 70 is not broken up and binned into the high- and low-energy bins, but is instead considered separately, as a transitional- or intermediate-energy bin separate from the high- and low-energy bins. Thus, a conventional generator waveform may be employed while still generating three-energy bins of data (e.g., high-, low-, and intermediate-) due to a different sampling scheme. In such an implementation, existing dual-energy hardware may be employed to obtain X-ray transmission data at three-energies using increased sampling (e.g., [low, intermediate, high, intermediate], [low, high, intermediate], or [low, intermediate, high], as opposed to just [low, high]).

It should be noted that, in a fast-switching X-ray tube context, such as in a system incorporating DRER circuitry, this transitional interval may be substantially reduced or eliminated, and instead a third, intermediate-energy level may be present. Thus, unlike the conventional generator waveform, when fast-switching voltage technology is employed, the intermediate-energy level may be held at a relatively constant kVp for some non-zero or non-transitional time interval between transitions to the next sequential high- or low-energy level. Such generator waveforms where the intermediate-energy level is maintained at a constant or steady kVp for an interval between transition may be more difficult to generate, but also more useful for multi-material decomposition.

Figure 3:
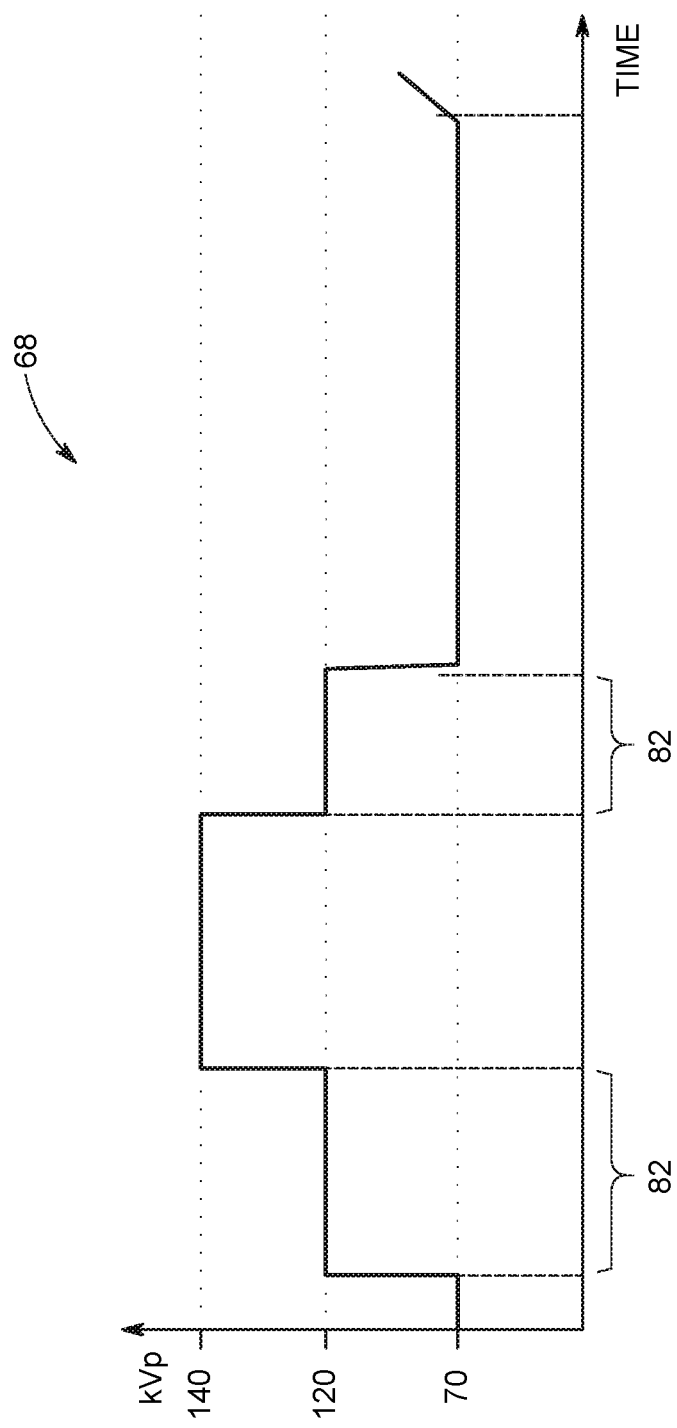
FIG. 3 depicts a fast-switched generator waveform in accordance with aspects of the present disclosure.

For example, turning to FIG. 3, a corresponding generator waveform 68 generated by a system using fast-switching voltage technology for all transitions is illustrated. In such an implementation, the hardware of the system 10 may be modified so as to include a second or duplicative fast-switching circuitry (e.g., energy recovery capacitors and associated circuitry and conductive paths), thereby allowing two-pairs of explicit fast-switching voltage operations, i.e., between low- and intermediate-energy and between intermediate- and high-energy. In this example, the transitions between energy levels are near-instantaneous, with the transitional or intermediate-energy instead being an explicit energy level that is switched to for an interval 82 using the fast-switching voltage technology. Thus, in such an implementation, the fast-switching circuitry may actually be reconfigured to transition between three (or more) energy levels instead of two. In particular, in such a fast-switching scenario, the X-ray source 12 may actually transition to a discrete, constant intermediate operating voltage (e.g., 105 kVp-120 kVp) for a time interval 82 before transitioning to the subsequent high- or low-operating voltage. In such a fast-switching context, the transition between operating voltages is not gradual, but is instead near instantaneous, such that the time interval 82 at the intermediate operating voltage is not an average over the course of the transition, but is instead a reflection of the actual, constant operating voltage over time interval 82.

With FIGS. 2 and 3 in mind, acquired projection data can be sampled into three bins, a low-energy bin, a high-energy bin, and an intermediate-energy bin, regardless of whether fast-switching voltage technology is employed or not. As will be appreciated, however, for each, low/high-energy acquisition period, the intermediate-energy data acquisition may occur over a single discrete time interval 82 or over two discrete time intervals 82, either of which may encompass a portion of the waveform in transition (e.g., a gradual rise or fall in kVp during the interval) or a near-constant kVp during the interval if fast-switching voltage technology is employed. While the preceding depict certain baseline generator waveforms representative of fast-switching and conventional voltage switching approaches that may be present in an imaging system 10, it should be appreciated that various other types of generator waveforms 68 may be generated which leverage the fast-switching circuitry and conventional switching approaches to generate hybrid waveforms or which disable the fast-switching circuitry to facilitate three energy level data acquisitions.

Figure 4:
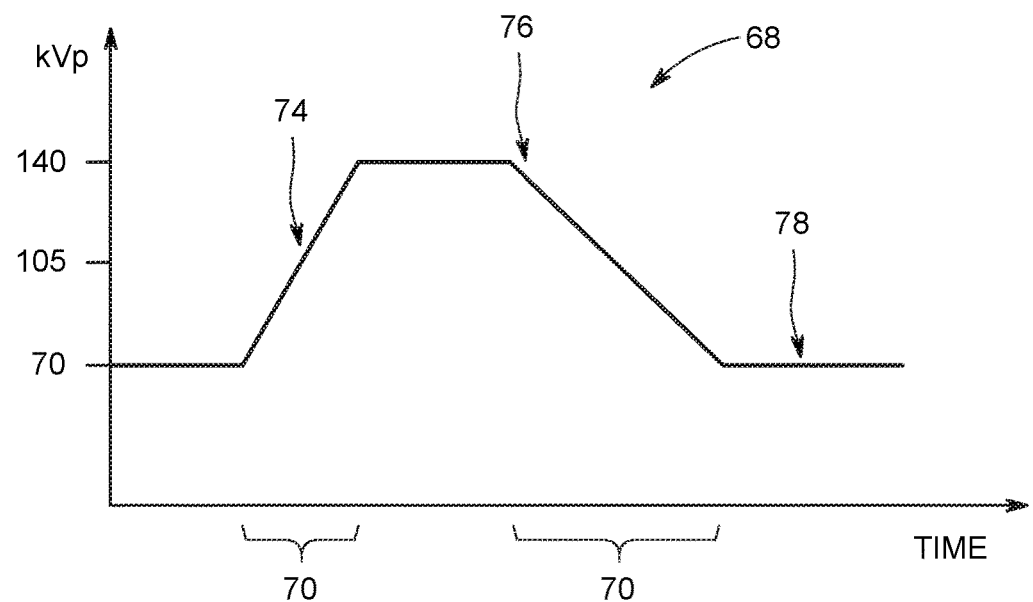
FIG. 4 depicts a slow-switched generator waveform and respective sampling times for acquiring X-ray transmission data at three different energy levels, in accordance with aspects of the present disclosure.

By way of example, and turning to FIG. 4, an example of a generator waveform 68 is illustrated which may be generated using a fast-switching (e.g., DRER) imaging system configured for dual energy imaging in which the fast-switching circuitry is disabled or otherwise turned off, effectively running the fast-switching system as a slow-switching system. In this example, due to the fast-switching circuitry being disabled, gradual or slow-switching transition intervals 70 are present. In one implementation in which the system 10 employs energy recovery (e.g., DRER) circuitry to implement fast-switching, the energy recovery circuitry may be disabled to allow non-fast transitions by charging the energy recovery capacitance to the mid-level between the high- and low-settings, opening the switches while the voltage is different from the mid-level, and closing the switches briefly in the middle of the transitions to make sure that the energy recovery capacitor does not discharge. The detector 28 may then be sampled four times during each cycle. e.g., once at the high-level, once at the low-level, and twice at the mid-level to acquire three energy levels of X-ray transmission data using a system 10 employing fast-switching circuitry configured for multi-energy acquisitions.

With respect to sampling X-ray data generated in accordance with the generator waveform 68 of FIG. 4, to obtain data corresponding to three energy levels, three sampling events (as opposed to the two sampling events that would typically occur in a dual-energy imaging scenario) may be performed. For example, in one implementation, sampling may occur with respect to the waveform 68 shown in FIG. 4 before or during (i.e., close in time to) the initial rise at time 74 (low-energy bin), close in time to the end of the high-energy plateau at time 76 (high-energy bin), and close in time to the end of the transition to low-edge plateau at the time 78 (intermediate-energy bin).

As used herein, the qualifier that a sampling event begins or ends close in time to a given transition may be understood to mean that the sampling event begins or ends within a time interval corresponding to +/−10% of the cycle duration (e.g., peak-to-peak, rise-time to rise-time, and so forth) with respect to the respective transition start or end point. This range recognizes the likelihood that certain of the benefits described herein may be captured even when sampling does not begin or end precisely at a given transition. Descriptions of the beginning or ending of sampling intervals as used herein, regardless of being otherwise described as occurring before, during or after, an event, should all be understood as being close in time to the event in this sense to allow both for intentional programmed timing of the sampling event as well as variations that may be present in both the X-ray generation and data sampling sub-systems. Thus, descriptions that a sampling event occurs before, during, or after a transition herein should also be understood by implication to signify that the sampling event occurs close in time to the referenced transition at least in this sense.

Figure 5:
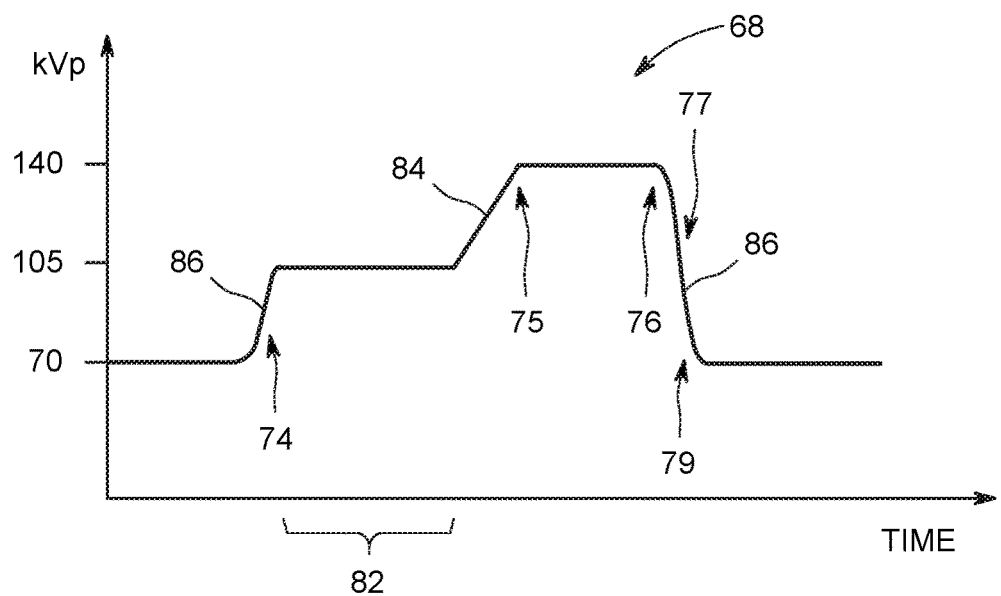
FIG. 5 depicts a generator waveform having both slow- and fast-switched transitions and respective sampling times for acquiring X-ray transmission data at three different energy levels, in accordance with aspects of the present disclosure.

Turning to FIG. 5, in a similar context, sampling at three energy levels may be performed using a system 10 having fast-switching circuitry by adding circuitry or modifying circuitry to make the triple kVp acquisition mode independent of tube current (mA). For example, the fast-switching circuitry may be modified or adjusted so as to store energy in a high-voltage tank circuit which is not supplemented at discharge so as to lead to only a partial rise at first (i.e., low- to intermediate-energy transition 86). In this or a similar manner, fast-switching may be employed selectively, such that some energy-level transitions are performed using fast-switching, while other energy-level transitions do not employ fast-switching and are performed more gradually. By way of this example, and as shown in FIG. 5, fast-switching may be employed twice (two out of three transitions), so as to provide an extended interval 82 at the intermediate-energy level. As a consequence, generator waveforms 68 may be generated that have both fast- and slow-switching characteristics, and which spend an interval 82 at a near-constant or constant intermediate kVp during one or both of the kVp rise or decay.

With this in mind, and turning to FIG. 5, in the depicted example a transition from low-energy to intermediate-energy (e.g., 105 kVp-120 kVp) is performed followed by a transition from intermediate-energy to high-energy, and high-energy to low-energy. In this example, the transition 84 from intermediate-energy to high-energy is not accelerated using the fast-switching circuitry, while the other transitions 86 are accelerated using fast-switching to be near or substantially instantaneous. The hardware change to facilitate such an enhanced fast-switching approach may be dissipative in nature, and may therefore benefit from additional thermal control measures or structures, such as the addition of a dissipative circuit.

With respect to sampling X-ray data generated in accordance with the generator waveform 68 of FIG. 5, to obtain data corresponding to three energy levels of data, the X-rays may be sampled in at least two different manners. In one scenario, the there may be four sampling events, with the intermediate-energy bin being sampled twice, once during kV rise and once during kV fall. For example, in one implementation, sampling may occur with respect to the waveform 68 shown in FIG. 5 before or during the initial rise at time 74 (low-energy bin), prior to the beginning of the high-energy plateau at time 75 (intermediate-energy bin, first), at the end of the high-energy plateau at time 76 (high-energy bin), and at the end of the kV fall at the time 79 (intermediate-energy bin, second). Conversely, in another scenario the intermediate bin may be sampled only once, such as during kV rise. For example, in such a scenario, sampling may occur with respect to the waveform 68 shown in FIG. 5 before or during the initial rise at time 74 (low-energy bin), prior to the beginning of the high-energy plateau at time 75 (intermediate-energy bin), and before or during the kV fall at the time 77 (high-energy bin).

Figure 6:
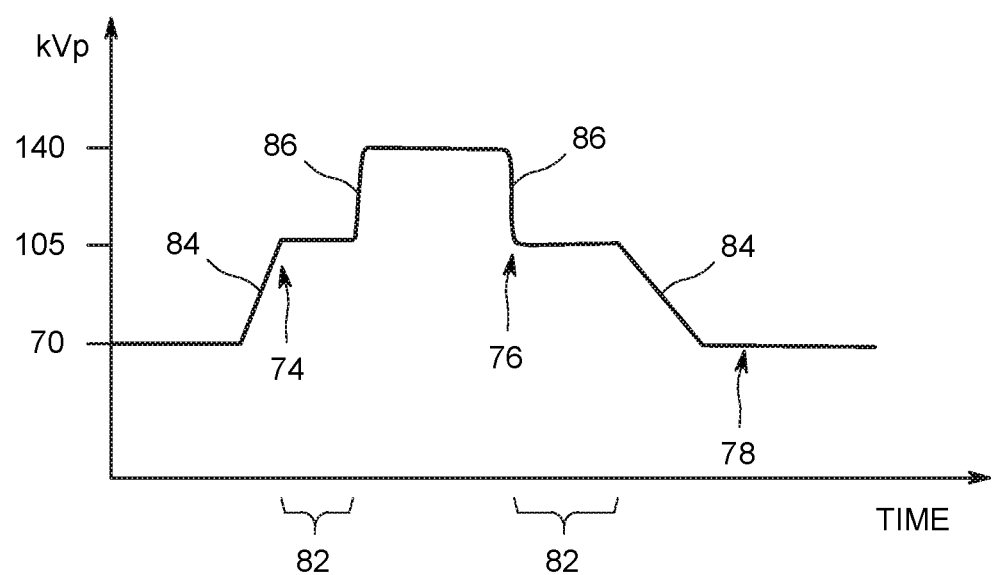
FIG. 6 depicts another generator waveform having both slow- and fast-switched transitions and respective sampling times for acquiring X-ray transmission data at three different energy levels, in accordance with aspects of the present disclosure.

A further hybrid generator waveform approach is shown with respect to FIG. 6. In this example, kV fall time control is employed as with the non-fast-switching scenarios to stabilize spectra independent of mA. The described hybrid generator waveform is discussed in greater detail in U.S. patent application Ser. No. 14/658,913, titled "Energy Imaging with Generally Constant Energy Separation" and filed on Mar. 16, 2015 to General Electric Company, which is herein incorporated by reference in its entirety for all purposes. In this example, fast-switching transitions 86 are employed only for the intermediate-energy to high-energy (and vice versa) transitions. Conventional (i.e., gradual) transitions 84 are employed for the low-energy to intermediate-energy (and vice versa) transitions. Thus, in such a scenario, the original fast-switching functionality between two energy levels is preserved (here between intermediate- and high-energy levels) with conventional switching employed to obtain the third energy level readings. Further, intermediate-energy spectra are maintained for time intervals 82, during which sampling may occur, as opposed to merely during a transitional ramp-up or ramp-down period.

With respect to sampling X-ray data generated in accordance with the generator waveform 68 of FIG. 6, to obtain data corresponding to three energy levels of data, the X-rays may be sampled using at least three sampling events, with the intermediate-energy bin being sampled once. For example, in one implementation, sampling may occur with respect to the waveform 68 shown in FIG. 6 before or during the initial rise at time 74 (low-energy bin), at the end of the high-energy plateau at time 76 (high-energy bin), and after or at the end of the kV fall to the low-energy plateau 78 (intermediate-energy bin).

Figure 7:
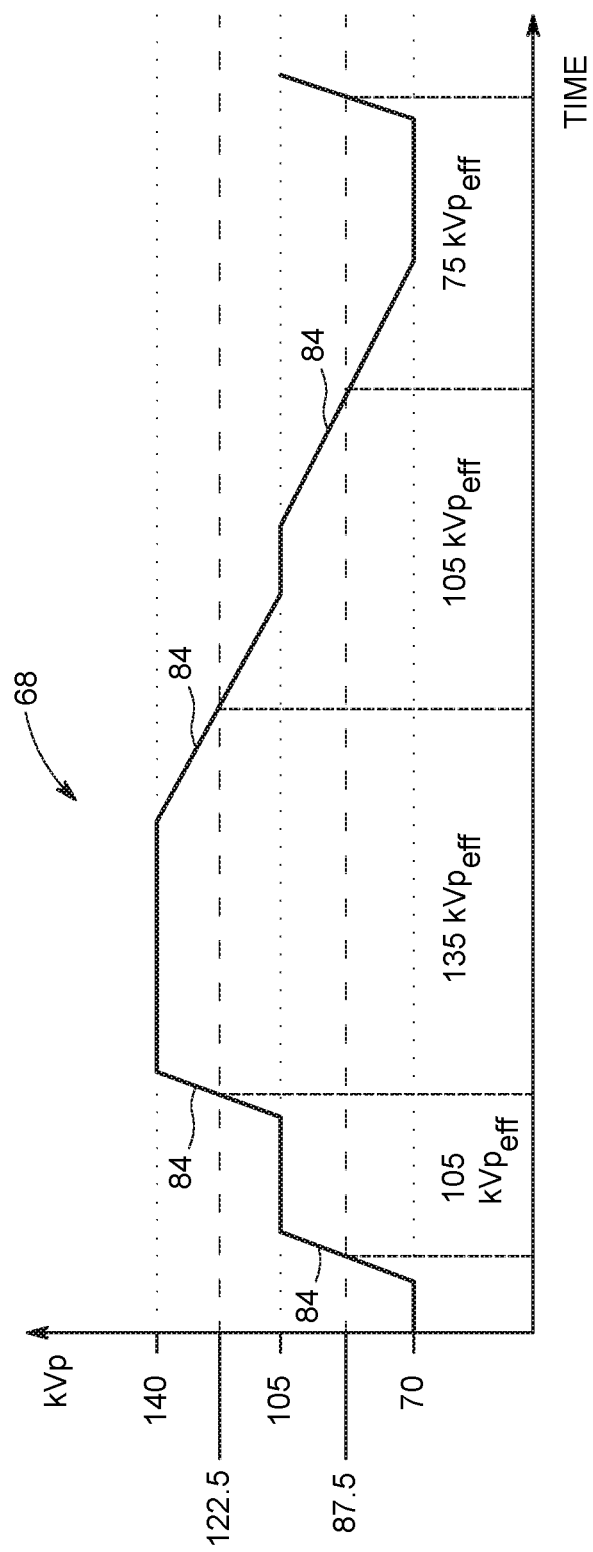
FIG. 7 depicts a slow-switched generator waveform and respective bin thresholds specified mid-transition, in accordance with aspects of the present disclosure.
Figure 8:
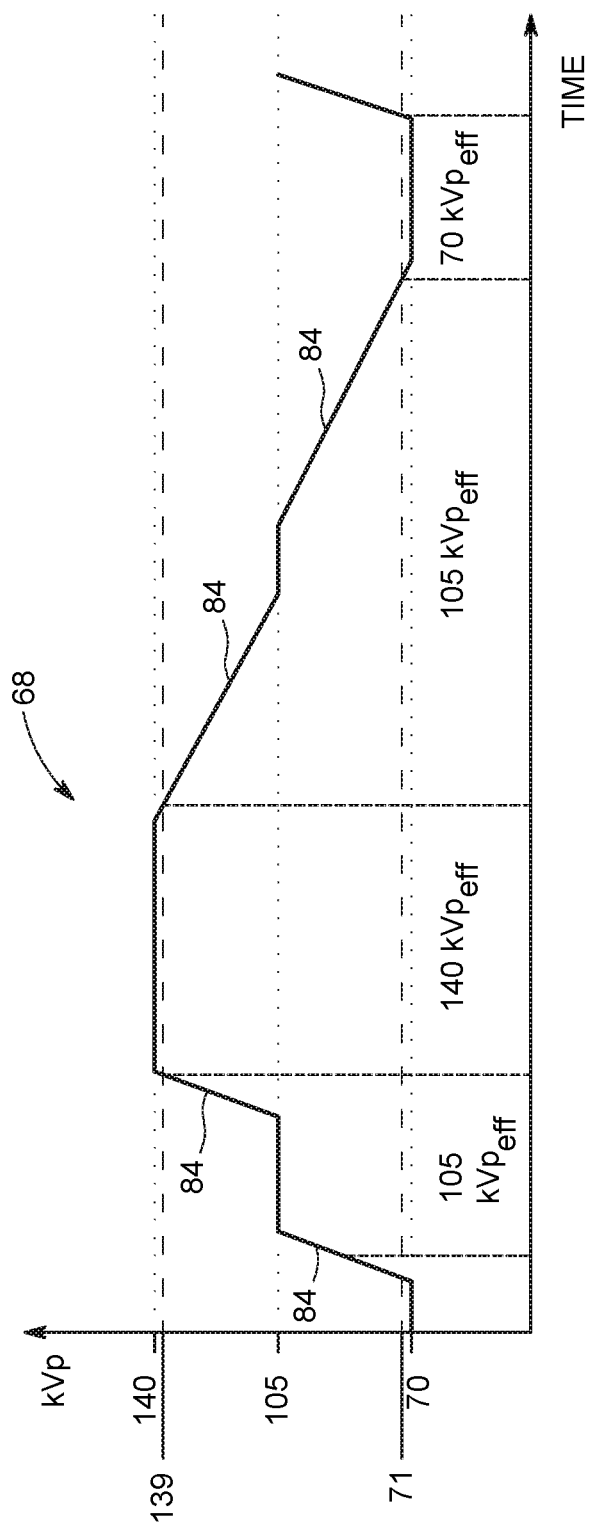
FIG. 8 depicts a slow-switched generator waveform and respective bin thresholds specified at transition edges, in accordance with aspects of the present disclosure.

With the preceding examples in mind, it may be worth noting that, instances where switching between energy levels is not fast (i.e., is not near instantaneous), selection of the break points between energy levels used in sampling may affect the observed average energy for a set of measurements. Turning to FIGS. 7 and 8, an example of this distinction is provided. In this example, FIG. 7 depicts energy bin break points (vertical dashed lines) defined at the center thresholds of each gradual transition 84. As a consequence, each "bin" corresponding to the low-, intermediate-, or high-energy levels has an average energy level near the central (i.e., intermediate) view that is the same as what would be observed in an instantaneous or fast-switching context (e.g., 105 kVp). However, the average energy level of the high- and low-energy views are degraded due to the slow-switching (i.e., gradual transitions 84), leading to effective or observed energies (e.g., 75 $kVp_{eff}$ and 135 $kVp_{eff}$) that do not correspond to the idealized scenario, which reduces the energy separation between the high- and low-energy views.

Conversely, turning to FIG. 8, in this same gradual or slow-switching context, setting the energy bin break points (vertical dashed lines) at the transition edges defined for the high- and low-energy plateaus or stable regions seen for each gradual transition 84, results in effective or observed energies comparable to what would be seen with fast-switching. As a consequence, each "bin" corresponding to the low-, intermediate-, or high-energy levels has an effective energy, on average, comparable to the instantaneous or fast-switching context, without degradation, (e.g., 70 kVp$_{eff}$, 105 kVp$_{eff}$, and 140 kVp$_{eff}$).

For both fast-switching and slow-switching contexts, the relative emission time spent at each energy level may be determined as a function of relative power (i.e., the integrated kVp×mA) for a given generator waveform 68. For example, in certain implementations, a power ratio of between 30% to 70% between kV$_{high}$ and kV$_{low}$ may be obtained. Similarly, in certain implementations: kV$_{high}$/kV$_{intermediate}$=kV$_{intermediate}$/kV$_{low}$ so as to obtain a suitable duty ratio.

Based on simulations and studies considering the present approaches, material separability using three energy bins (i.e., low, intermediate, and high) is believed to be comparable using both the slow- and fast-switching approaches as described herein. In particular, image quality metrics in the form of contrast-to-noise ratios were calculated using three-energy binning as discussed herein. These ratios were found to be generally comparable between slow- and fast-switching implementations using pairwise comparisons of spectra (e.g., low to intermediate, intermediate to high, or low to high). By way of example, slow- and fast-switching techniques in combination with triple-energy binning yielded similar material separability for iodine, though fast-switching yielded better material separability for k-edge material contrast (e.g., tantalum) imaging.

The preceding describes various generator waveform and sampling scenarios that may be employed to obtain X-ray transmission data for three energy levels. However, certain related approaches may be employed to enhance or improve dual-energy material decomposition protocols as well. For example, triple kVp (i.e., three energy) sampling may be used for de-noising of the dual-energy material decomposition reconstructions and/or for improving image registration or alignment processes.

In the de-noising context, it may be appreciated that the sampled intermediate-energy data adds little to the dual-energy material decomposition process as those energies close to the transitions thresholds (which may be sampled as intermediate-energy data) add noise, but otherwise add little useful energy information. Thus, cleaner or more useful spectral data may be obtained without this intermediate-energy data associated with the transitions. By excluding the intermediate-energy data from the material decomposition processing (as discussed below), the separation between the high- and low-energy sampled data is improved, which in turn improves the material decomposition process.

Figure 9:
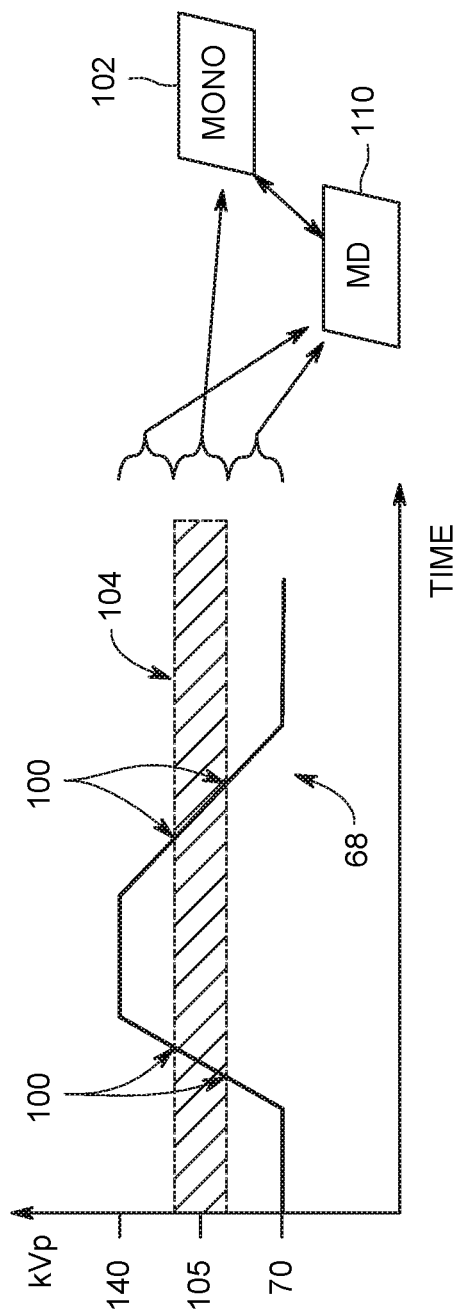
FIG. 9 depicts a generator waveform and corresponding X-ray transmission sampling at three energy levels, where the intermediate-energy data is not separately used in a material decomposition process, in accordance with aspects of the present disclosure.

With this in mind, for a given multi-energy X-ray generation sequence, one or more intermediate bins of X-ray transmission data may be sampled, such as at times 100 with respect to the sample generator waveform 68 shown in FIG. 9. The intermediate-energy data 104 may be excluded from the material decomposition processing (i.e., subtractive processing) and instead processed to generate a monochromatic or generally (i.e., not fully) monochromatic image 102 based on the energy range (e.g., 100 kVp-110 kVp, 95 kVp-115 kVp, and so forth) represented in the intermediate-energy bin. By way of example, the monochromatic image 102 may be generated by summing (with or without weighting) the intermediate-energy data acquired and using the aggregated intermediate-energy data to generate a generally monochromatic image 102, such as a black-and-white image. In such an implementation, while the intermediate-energy values may be used to generate the monochromatic image, they need not be used exclusively. For example, measurements from one or both of the high- and low-energy ranges may also contribute to the computation of the monochromatic image.

This monochromatic image 102 data may then be averaged or blended with the monochromatic material decomposition (MD) images 110 generated from the high- and low-energy data to lower the noise in the resulting images. Such an approach may employ intermediate-energy data sampled during the kV rise, the kV decay, or both (as shown in FIG. 9) and may use the same or different thresholds in instances where the rise and decay are both sampled. Identical thresholds are shown in FIG. 9 for simplicity.

In addition, in a further implementation the intermediate-energy views generated using the intermediate-energy data may be used to improve the interpolation and/or registration of the high- and/or low-energy views as they neighbor the highest-energy samples of the low-energy data and the lowest-energy samples of the high-energy data. This improved interpolation and/or registration may help improve the resolution of the respective high- and low-energy images that may be attributable to loss of spatial information due to gantry rotation. In particular, since the intermediate-energy bins are double-sampled relative to the respective high- and low-energy bins, images generated using the combined (i.e., summed) and/or averaged intermediate-energy data will typically be at a higher resolution than those generated using the high- or low-energy data alone. The higher-resolution intermediate-energy image may therefore be used recover detail in the high- and low-energy reconstructions.

Lastly, though the preceding discussion and examples relate various binning and sampling strategies that may be generally applicable to the present approaches, it should also be appreciated that the sampling and binning strategies may be optimized for any of the preceding approaches, such as to best suit a given material triplet (or quadruplet) for which separation is desired. Optimization of the energy levels and cut-off points defining each bin may result in corresponding optimization of the duty cycle associated with a corresponding generator waveform 68.

For example, the optimum energy of each bin (and the respective thresholds or cutoff points defining the respective bin) may encompass a region of relatively constant kVp with respect to a generator waveform 68 (e.g., a flat or plateau region), a combination or range of changing kVp (e.g., a gradual transition region), or a combination of such regions. Part of the optimization process may involve, based on the material(s) for which separation is sought, optimizing the relative flux associated with one or more of the respective energy bins.

Technical effects of the invention include acquiring X-ray transmission data for at least three energy levels using fast-switching, slow-switching, or a combination of fast and slow switching to transition between X-ray energy levels.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An X-ray generator waveform used in generation of X-rays having at least three distinct energy levels, comprising:
    a low-energy level having a substantially constant low operating voltage value for at least a first duration;
    at least one intermediate-energy level having a substantially constant intermediate operating voltage value for at least a second duration; and
    a high-energy level having a substantially constant high operating voltage value for at least a third duration,
    wherein X-ray data corresponding to the X-ray generator waveform is sampled during at least three separate and distinct data sampling voltage intervals during each operating voltage rise and decay cycle, and wherein the at least three separate and distinct data sampling operations comprise:
        sample close in time to a start of the operating voltage rise cycle at a low-energy interval of the generator waveform to generate a low-energy set of data;
        sample a transition close in time to an end of the operating voltage rise cycle from the low-energy level to the high-energy level once to generate a first subset of intermediate-energy data;
        sample close in time to a start of a kV decay cycle at a high-energy interval of the generator waveform to generate a high-energy set of data; and
        sample a transition close in time to an end of operating voltage decay cycle from the high-energy level to the low-energy level once to generate a second subset of intermediate-energy data.

2. The X-ray generator waveform of claim 1, wherein transitions between each energy level are all near instantaneous.

3. The X-ray generator waveform of claim 1, wherein some transitions between energy levels are near instantaneous and the remainder of the transitions between energy levels are gradual.

4. The X-ray generator waveform of claim 1, comprising two distinct intermediate-energy levels having substantially equal operating voltages.

5. The X-ray generator waveform of claim 1, wherein transitions between the low-energy level and a respective intermediate-energy level are gradual while transitions between the respective intermediate-energy level and the high-energy level are near instantaneous.

6. The X-ray generator waveform of claim 1, wherein:
    a first transition between a respective intermediate-energy level and the high-energy level is gradual;
    a second transition between the low-energy level and respective intermediate-energy level is near instantaneous; and
    a third transition between the high-energy level and the low-energy level is near instantaneous.

7. A method for sampling X-ray data, comprising:
    generating X-rays in accordance with an X-ray generator waveform having an operating voltage rise and decay cycle that is repeated over time, wherein the X-ray generator waveform has a high-energy level and a low-energy level and gradual transitions between the high-energy level and low-energy level; and
    sampling data during at least three separate and distinct data sampling voltage intervals during each operating voltage rise and decay cycle, wherein the at least three separate and distinct data sampling operations comprise:
        sampling at least twice, at least once close in time to a start of the operating voltage rise cycle and at least once close in time to an end of the operating voltage rise cycle of the generator waveform to generate a low-energy set of data and an intermediate-energy set of data; and
        sampling at least once close in time to a start or an end of the operating voltage decay cycle, including during the operating voltage decay cycle, of the generator waveform to generate a high-energy set of data.

8. The method of claim 7, wherein operating voltages of the X-ray generator waveform are substantially constant during at least one of the separate and distinct data sampling intervals.

9. The method of claim 7, wherein operating voltages of the X-ray generator waveform are substantially constant during at least two of the separate and distinct data sampling intervals.

10. The method of claim 9, wherein a respective sampling interval in which the operating voltage is substantially constant corresponds to the highest operating voltage or the lowest operating voltage of the operating voltage rise and decay cycle.

11. The method of claim 9, wherein two respective sampling intervals in which the operating voltage is substantially constant correspond to the highest operating voltage and the lowest operating voltage of the operating voltage rise and decay cycle.

12. A method for generating material decomposition images, comprising:
    acquiring X-ray transmission data at a low-energy, a high-energy, and an intermediate-energy, using sampling, wherein the sampling comprises sampling X-ray transmission data during at least three separate and distinct data sampling voltage intervals during each operating voltage rise and decay cycle, and wherein the at least three separate and distinct data sampling operations comprise:
        sampling at least once close in time to a start or an end of the operating voltage rise cycle, or during the operating voltage rise cycle, of a generator waveform to generate a low-energy set of data;
        sampling at least twice, at least once close in time to a start of the decay cycle of the generator waveform and once close in time to an end of the decay cycle, to generate a high-energy set of data and an intermediate-energy set of data;
    generating one or more material decomposition images using the low-energy set of data and the high-energy set of data; and
    correcting at least one material decomposition image with the intermediate-energy set of data.

13. The method of claim 12, wherein the step of correcting comprises compensating for or removing noise from the one or more material decomposition images using the intermediate-energy set of data.

14. The method of claim 12, wherein the step of correcting comprises recovering spatial detail into the one or more material decomposition images using the intermediate-energy set of data.

15. The method of claim 14, wherein recovering spatial detail is performed using a high-resolution image generated at least from the intermediate-energy set of data, and wherein the intermediate-energy set of data is acquired during both a low-to-high operating voltage transition and a high-to-low operating voltage transition.

16. The method of claim 12, wherein the step of correcting comprises generating a substantially monochromatic image using at least the intermediate-energy set of data and using the monochromatic image to correct the at least one material decomposition image.

17. The method of claim 16, wherein the substantially monochromatic image is generated using one or both of the low-energy set of data or the high-energy set of data in addition to the intermediate-energy set of data.

\* \* \* \* \*